(12) United States Patent
Stern

(10) Patent No.: US 8,420,573 B2
(45) Date of Patent: Apr. 16, 2013

(54) COMB POLYMER DERIVATIVES OF POLYETHERAMINES USEFUL AS AGRICULTURAL DISPERSANTS

(75) Inventor: Alan J. Stern, Magnolia, TX (US)

(73) Assignee: Huntsman Petrochemicals LLC, The Woodlands, TX (US)

( * ) Notice: Subject to any disclaimer, the term of this patent is extended or adjusted under 35 U.S.C. 154(b) by 0 days.

(21) Appl. No.: 13/530,379

(22) Filed: Jun. 22, 2012

(65) Prior Publication Data

US 2012/0264610 A1  Oct. 18, 2012

Related U.S. Application Data

(62) Division of application No. 11/726,200, filed on Mar. 15, 2007, now Pat. No. 8,247, 353.

(60) Provisional application No. 60/782,430, filed on Mar. 15, 2006.

(51) Int. Cl.
*A01N 37/00* (2006.01)
*A01N 37/10* (2006.01)
*A01N 33/00* (2006.01)

(52) U.S. Cl.
USPC ............................. 504/320; 504/321; 504/326

(58) Field of Classification Search .................. None
See application file for complete search history.

(56) References Cited

U.S. PATENT DOCUMENTS

| | | | |
|---|---|---|---|
| 5,393,343 A | 2/1995 | Darwin et al. | |
| 5,410,017 A * | 4/1995 | Bortnick et al. | ............... 528/363 |
| 5,612,396 A | 3/1997 | Valenti et al. | |
| 6,017,994 A | 1/2000 | Carter et al. | |
| 6,406,138 B1 | 6/2002 | Gore | |
| 6,528,593 B1 | 3/2003 | Eiffler et al. | |
| 6,723,880 B2 | 4/2004 | Neumann et al. | |
| 6,767,865 B2 * | 7/2004 | Den Tandt et al. | ............. 504/362 |
| 6,844,293 B1 * | 1/2005 | Kirby et al. | ................ 504/116.1 |
| 6,855,763 B1 | 2/2005 | Kirby et al. | |
| 6,894,107 B2 | 5/2005 | Gore | |
| 7,109,267 B2 | 9/2006 | Kirby et al. | |
| 7,179,859 B2 | 2/2007 | Kirby et al. | |
| 7,241,729 B2 | 7/2007 | Sivik et al. | |
| 7,683,120 B2 | 3/2010 | Thetford et al. | |
| 2003/0225168 A1 | 12/2003 | Deroo et al. | |
| 2005/0256005 A1 | 11/2005 | Reekmans et al. | |

FOREIGN PATENT DOCUMENTS

WO  02/19821  3/2002

* cited by examiner

*Primary Examiner* — Alton Pryor

(74) *Attorney, Agent, or Firm* — Huntsman International LLC

(57) ABSTRACT

This invention concerns novel dispersants that are the reaction products of succinic anhydride-containing resins with certain amines. These water soluble dispersants have been found to be unique and highly effective dispersants for water insoluble agricultural suspension concentrate formulations.

26 Claims, No Drawings

COMB POLYMER DERIVATIVES OF POLYETHERAMINES USEFUL AS AGRICULTURAL DISPERSANTS

CROSS REFERENCES TO RELATED APPLICATIONS

This application is a divisional of currently pending U.S. patent application Ser. No. 11/726,200, which is the National Phase of International Application PCT/US2007/06440, filed Mar. 15, 2007, which designated the U.S. and which claims priority to U.S. Provisional Application Ser. No. 60/782,430, filed Mar. 15, 2006. The noted applications are incorporated herein by reference.

TECHNICAL FIELD

This invention concerns the reaction products of succinic anhydride-containing resins (e.g. polyisobutenyl succinic anhydride (PIBSA) and/or styrene maleic anhydride (SMA)) with certain amines. These products have been found to be unique and highly effective dispersants for agricultural suspension formulations.

BACKGROUND

Many different classes of dispersants are known. Many different types of dispersants are needed because of the wide range of materials that need to be dispersed in liquid. Agricultural chemicals vary widely in structure and are difficult to disperse at high concentration in water in many cases. There exists a difficulty in making high solids, low viscosity dispersions of solids in water or other liquids. Suspension formulations of agriculturally useful chemicals are often the preferred formulation type for many products due to the ease of manufacture, distribution, and use. Modern agricultural practices are reliant upon these formulations for the control of undesirable vegetation, insects, diseases, and for the enhancement of crop productivity through the application of plant growth regulators, micronutrients and macronutrients. The present invention expands the utility of suspension formulations by providing novel dispersants for a wide variety of agriculturally useful chemicals, as well as methods for their use.

SUMMARY OF THE INVENTION

This invention addresses the disadvantages and/or shortcomings discussed above of current dispersants. The newly invented dispersants are typically lower cost, easier to manufacture, and more efficacious in many applications. There is a need for better dispersants for agricultural chemicals so that higher levels of solids can be dispersed more easily and have a longer shelf life, thereby leading to cost savings for the manufacturer.

In one broad respect, this invention is an agricultural composition comprising: a water soluble dispersant comprising a reaction product of at least one succinic anhydride-containing resin and at least one amine; and at least one water insoluble agricultural agent. The reaction product is generally of low molecular weight such as 5000 to 15000 and typically is formed from a polyether monoamine. The reaction product is water soluble and functions as a dispersant for the agricultural agent. The agricultural agent can vary widely. In general, the agricultural agent is an active component such as a pesticide including but not limited to herbicides, insecticides, fungicides, and so on.

Typically, the composition comprises from about 0.5% to about 4% of the dispersant. A typically formulation will contain the active ingredient(s) in an amount of from about 10% to about 50% by weight of the formulation, and other formulants such as wetting agent(s) typically in an amount of 0 to about 3% by weight of the formulation, antifreeze agent(s) in an amount from about 0 to about 10% by weight of the formulation, antisettling agent(s) in an amount of 0 to about 10% by weight of the formulation, and antifoaming agent(s) in an amount of 0 to about 1% by weight of the formulation, and the balance water. The composition may be in the form of a concentrate which may optionally contain water. During use, the concentrate is diluted in water to form, for example, a sprayable composition. This composition typically contains the active, water, and the dispersant. Adjuvants to improve the pesticide's performance can be present. They may be included in the pesticide formulation or added to the dilute solution used for spraying. Adjuvants take many forms, for example: surfactants, water conditioning agents, drift reduction agents, and so on.

In another broad respect, this invention is a process for making a dispersed agricultural agent composition, comprising: mixing a water soluble dispersant comprising a reaction product of at least one succinic anhydride-containing resin and at least one amine with at least one water insoluble agricultural agent to form the composition. If necessary, the particle size of the agricultural agent may be reduced by milling a slurry of the composition. Preferably, the particles of agricultural agent have a median size of about 1-5 microns.

In another broad respect, this invention is a process of treating a substrate, comprising: diluting with water a concentrated composition comprising a water soluble dispersant comprising a reaction product of at least one succinic anhydride-containing resin and at least one amine and at least one water insoluble agricultural agent to form an aqueous composition, and applying the aqueous composition to the substrate. The composition can be applied by spraying, pouring, painting, and so on. The substrate can be soil, a plant, a fungus, an insect, and so on. The substrate could also include structures (e.g., buildings) in the case of insect control.

In another broad respect, this invention is a composition produced by the process of providing a first component that comprises the reaction product of at least one succinic anhydride-containing resin and at least one amine; providing a second component comprising at least one agricultural agent; and contacting the first component and second component.

DETAILED DESCRIPTION

High solids, low viscosity, stable dispersions of agrochemicals can be made with dispersants derived from succinic anhydride containing resin reacted with amines such as JEFFAMINE® amines. JEFFAMINE is a registered trademark of Huntsman Corporation.

In general, the amines used in the practice of this invention are water-soluble or water-dispersable, and form the hydrophilic portion of the dispersant. Without such a hydrophilic portion the resulting compound would not be capable of forming a water soluble disperant.

The polyether amines that can be used in the practice of this invention include JEFFAMINE® amines including but not limited to XTJ-506, XTJ-507, M-2070, and the like, available from Huntsman Corporation. In an embodiment, the JEFFAMINE® amine is a polyether monoamine. Polyether monoamines are well known in the art. The polyether portion of the polyether monoamine typically contains an alkylene oxide portion such as derived from ethylene oxide (EO), propylene oxide (PO), butylene oxide, and combinations thereof. Frequently, the polyether polyamines contain combinations of EO and PO. The polyether monoamines can contain 100% of a given alkylene oxide or may contain two or more different alkylene oxides. In general the polyether monoamines used in the practice of this invention have molecular weights in the range from about 500 to about 2500. The polyether monoamines are preferred in the practice of this invention. The polyether monoamines typically are of the formula:

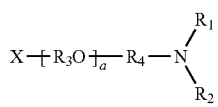

in which $R_1$ and $R_2$ are each independently hydrogen, and X is selected from the group consisting of: hydrogen; an alkyl group having from about 1 to about 22 carbon atoms, including all integers in between, whether straight-chain, branched, or cyclic; a hydroxyl group, a hydroxy terminated group, and any other non-amine terminated group. $R_3$ and $R_4$ are in each occurrence a straight-chain or branched alkyl or bridging group or alkylene group and a is any integer between 0 and 400.

In some embodiments of the present invention, the amine used to make the dispersant has multiple amine groups. In other embodiments, a given product can contain some low molecular weight amines such as dimethylaminepropylamine, butylamine, morpholine, ammonia and the like, provided that the resulting product still serves to function as a dispersant. One skilled in the art, with the benefit of this disclosure will recognize other appropriate amines to use in embodiments of this invention.

The succinic anhydride-containing resins that can be used in the practice of this invention include resins containing aromatic moieties, aliphatic moieties, and combinations thereof. The at least one succinic anhydride-containing resin provides the backbone for the dispersant. For example, styrene maleic anhydride (SMA) resins (which may also be referred to as poly(styrene-co-maleic anhydride) can be employed, which have aromatic groups and succinic anhydride groups in the final resin. Generally, SMA resins are made with up to about 50% mole percent maleic anhydride, typically in the range from about 20% mole percent to about 50% mole percent anhydride. Sources of anhydride moieties in the resins include anhydride-containing compounds that also contain double bonds that can undergo polymerisation, for example maleic anhydride, itaconic anhydride, citraconic (methylmaleic)anhydride, ethylmaleic anhydride, 1,2-cyclohexene-1,2-dicarboxylic acid anhydride and 1,2-cyclohexene-4,5-dicarboxylic acid anhydride, of which maleic anhydride is preferred. While styrene containing copolymers are readily available and preferred for use with some agricultural agents, they are not universally the best. Other copolymers are preferred in some instances as illustrated by the examples contained herein. Other monomers can be used to make the resin such as styrene substituted with a lower alkyl group having up to 18 carbon atoms, in one embodiment up to 6 carbon atoms, such as methylstyrene and butylstyrene. Other possible unsaturated copolymerisable monomers that may be present, in place of or in addition to styrene, include olefins such as ethylene, conjugated dienes such as 1,3-butadiene and isoprene, alkyl acrylates and methacrylates, especially lower alkyl such as methyl, ethyl and, preferably, the butyl and ethylhexyl esters, vinyl acetate, acrylonitrile, methacrylonitrile, acrylamides, methacrylamides and unsaturated ethers such as alkyl vinyl ethers, for instance, the methyl and ethyl ethers. Thus, in certain embodiments, the succinic anhydride-containing resin may include at least one acrylic acid such as methylacrylate, acrylonitrile, derivatives thereof, and combinations thereof. Also mentioned are the vinyl sulphoxides and vinyl sulphones. Mixtures of these can be used in the copolymerization to design copolymers that have particular solubility properties and, when reacted with polyamine or polyol, impart particular properties to the dispersant formed. Likewise, aliphatic resins such as olefin-based resins such as but not limited to polyisobutenyl succinic anhydride (PIBSA) resins. Olefins other than isobutenyl can be employed to make such resins, including combinations of olefins. For example, olefins such as ethylene, propylene, butylene, pentene, hexane, heptane, and so on, can be employed. In general, suitable resins are of low molecular weight to keep the overall molecular weight of the final dispersant relatively low (e.g., 5000-15,000) so that the disperant remains relatively water soluble. One skilled in the art, with the benefit of this disclosure will recognize other monomers that can be used in succinic anhydride-containing resins of this invention.

The solvents that are used in the practice of this invention to prepare the dispersants are nonreactive toward the resin and the amine. In general, the solvent is aprotic. For example, the solvent can be aromatic solvents such as benzene and alkylbenzenes such as toluene and xylene, ethers such as methyl t-butyl ether, ketones such as methylisobutylketone, esters such as ethyl acetate, propyl acetate, carbonates such as ethylene carbonate, propylene carbonate, and butylene carbonate, halogenated aliphatic hydrocarbons such as dichloromethane, lactones such as butyrolactone, and aliphatic nitriles such as butyronitrile. Mixtures of solvents can be used. There can also be used cosolvents to change the properties of solvents or solvent mixtures. The solvent is used in sufficient quantities to dissolve the resin and, optionally, the water soluble dispersant of this invention. The amount of solvent used can vary widely and will be any amount suitable for making the reaction product, as is apparent to one of skill in the art.

The desired reaction product of the anhydride with the amine can be referred to as an amic acid (or "half amide"). Because the reaction product may form a polymer having more than one amic acid group, the reaction product may be a polyamic acid. In addition to the half amide, the amic acid also has a carboxylic acid functional group. This reaction product can be achieved at relatively mild reaction temperatures as a result of the high reactivity of the anhydride linkage. Temperatures of less than 100 degrees Celsius (C.), preferably less than 60C are sufficient to convert the anhydride to the amic acid when the amine is present. At higher reaction temperatures, it is possible to form an imide by condensation and elimination of water. While imide formation is not harmful to the performance of the resulting product, it is not the object of this invention to form imides.

In one embodiment of the present invention, the carboxylic acid group(s) that are part of the amic acid or polyamic acid reaction product are either partially or wholly neutralized. These carboxylic acid groups may be neutralized by sodium, potassium, calcium, ammonia, other alkylamines or other neutralization chemicals known by those skilled in the art. By leaving the carboxylic acid groups alone or by partially or wholly neutralizing the carboxylic acid groups, one skilled in the art may be able to fine tune an agricultural composition for a particular application.

The dispersants can be made by dissolving the succinic anhydride containing resin (e.g., SMA™ resin which is available commercially from Sartomer Company of Exton, Pa., SMA is a mark used by the Sartomer Company) in a non-reactive solvent such as propylene carbonate, and reacting with the desired JEFFAMINE® amines to make the amic acid. The resin and solvent may be heated to about 60C prior to the addition of the amine to thereby facilitate a more rapid reaction. The order of addition is not believed to be critical and as such the anhydride resin can be added to the amine. Typically, stoichiometric amounts of amine are added relative to the amount of anhydride in the resin. However, it is believed that more or less than stoichiometric amounts of amine can also form an excellent dispersant. The reaction product can be isolated and purified, as desired, using techniques well known to those of skill in the art. The reaction product of these materials have the desirable "comb" structure in which the resin forms the backbone of the comb and the JEFFAMINE® amine makes up the "teeth" of the comb, i.e., the polyether portion of the amine forms a hydrophilic portion of the reaction product. This comb architecture is desirable because of its ability to efficiently stabilize suspended particles. These dispersants are then used as formulants in agricultural chemical suspension concentrates. The dispersants of this invention have been found to effectively reduce the viscosity of concentrated suspensions while helping to reduce the tendency of the suspended particles to settle out, a process known as sedimentation, for a wide variety of pesticides.

The molecular weight ($M_w$) of the reaction products may range from 5000 to 20,000. The molecular weight can be measured using, for example, gel permeation chromatography using a polyethylene glycol standard. The new dispersants are very light colored and do not impart noticeable color to the formulations they are used in. In contrast, other commercial dispersants, for example ligninsulfonates, are very dark and therefore result in brown formulations when used.

It may be true also that the new materials can be used at lower rates than existing dispersants such as alkylnaphthalene sulfonate formaldehyde condensates like MORWET® D-425 liquid dispersant commercially available from Akzo Nobel Specialties Inc. of Chicago, Ill. MORWET is a registered trademark of Akzo Nobel Specialties Inc.

The new dispersants may be easier to make than other comb polymer type dispersants, such as TERSPERSE® 2500 dispersant and TERSPERSE® 2700 dispersant, because succinic anhydride resins are readily commercially available (for example, SMA® resin from Sartomer Company of Exton, Pa. and OLOA® 15500 ashless dispersant intermediate from Chevron Oronite LLC of Houston, Tex.). TERSPERSE is a registered trademark of Huntsman Petrochemical Corporation. OLOA is a registered trademark of Oronite Chemical Company.

Embodiments of the present invention disclose an agricultural composition comprising a reaction product of at least one succinic anhydride-containing resin and at least one amine. The at least one succinic anhydride-containing resin and at least one amine form a comb-like dispersant.

The invention provides for a range of dispersants with varying properties, resulting from the choice of amine and the choice of succinic anhydride containing resin. Those skilled in the art of preparing suspension concentrate formulations will be able to easily select the best set of reactants to prepare the optimum dispersant for the material to be dispersed.

Embodiments of the present invention include an active agricultural agent. In general the agricultural agent has low water solubility such as less than ½% water solubility at room temperature and, furthermore, generally has a melting point of at least 60C, more typically at least 70C, and preferably at least 80C. This agent may be herbicides, pesticides, fungicides, pest-related materials, plant growth regulators, micronutrients, macronutrients, or other active or inactive ingredients used in the agriculture industry. The agents used in the examples below are representative and not necessarily intended to be limiting as to the scope of this invention. In one embodiment, the agricultural agent is suspended in an aqueous fluid. In another embodiment, the agricultural agent is suspended in a non-aqueous fluid. One skilled in the art, with the benefit of this disclosure will recognize appropriate agricultural agents to be used in embodiments of this invention.

In other embodiments, the contacting of the first component and second component occurs in a liquid continuous phase. One skilled in the art will recognize other suitable methods of contacting the first and second component Although dispersants disclosed in this specification specify their use with agricultural agents, other applications may include pigment dispersants for paint, dye or ink formulations and use as a superplasticizer for cement or wallboard.

The following examples are illustrative of the present invention and not intended to be limiting as to the scope of the invention or the claims hereto. Unless otherwise denoted, all amounts are parts by weight.

Example 1

Part 1.

A solution of butyrolactone (20.9 parts) and SMA-1000 (10.4 parts) was prepared by mixing the materials at 45 C for 12 hours under a dry atmosphere. To this solution was added JEFFAMINE® 507 amine (89.5 parts) with continued stirring for 15 minutes to form a reaction product of the amine and the SMA, which may be referred to as the dispersant. A formulation containing the fungicide mancozeb (manganese ethylenebis(dithiocarbamate) (polymeric) complex with zinc salt) was made from TERWET® 1004 alpha olefin sulphonate surfactant (1 part) (TERWET is a registered trademark of Huntsman Petrochemical Corporation), the dispersant (3 parts), ethylene glycol (4 parts), water (36 parts), and mancozeb (56 parts). This was blended by hand and resulted in a thin, pourable suspension.

Part 2.

In contrast to Part 1, a blend identical to the above, but using dispersant MORWET® D-425 dispersant in place of the Dispersant 8321-100C, was made by the same technique. The result was a paste that was non-pourable.

Part 3.

To further demonstrate the utility of Dispersant 8321-100C, a blend containing no dispersant was prepared as follows: water (40 parts), TERWET® 1004 surfactant (1 part), ethylene glycol (5 parts) and mancozeb (54 parts). Due to the lack of Dispersant 8321-100C, the result was a paste that would not flow and was very difficult to mix.

Example 2

A comb polymer dispersant was prepared from PIBSA and JEFFAMINE® XTJ-506 amine by reacting 57 parts PIBSA (commercially available from Chevron Oronite under the name OLOA® 15500 ashless dispersant intermediate) with 43 parts JEFFAMINE® XTJ-506 amine. The reaction was accomplished by combining and mixing vigorously the two components while heating the mixture to 60° C. The reaction product was subsequently diluted with 100 parts propylene glycol to give a blend that contained 50% active dispersant on a wt. basis.

Dispersant test: To a mixture of water (40 parts), ethylene glycol (5 parts), SURFONIC® L24-7 wetting agent (available from Huntsman Corporation, SURFONIC is a registered trademark of Huntsman Petrochemical Corporation) (2 parts) and the above PIBSA/JEFFAMINE dispersant (3 parts), was added captan technical fungicide (50 parts). This blend was homogenized with a high-shear mixer, yielding a thin, pourable suspension.

In contrast, in a separate experiment, the PIBSA/JEFFAMINE dispersant was replaced with dispersant MORWET D-425 dispersant (available from Akzo-Nobel), a high viscosity suspension was obtained.

Example 4

In this example, a number of agricultural compositions were prepared using the dispersants of this invention. To expedite the preparation of the large number of unique samples needed, a working stock suspension of each active was prepared and milled until an average particle size of 3-4 microns was achieved. This stock suspension was composed of technical active (48 parts), wetting agent (1 part), and water (49.75 parts). "Room" was left for 1.25 parts by weight of dispersant to be added later. Each stock suspension was divided into eight portions of 125 grams. Each dispersant in the study was added to one of the suspension subsamples such that 1.56 grams of dispersant on an active weight basis was used. The dispersant was incorporated with the use of a high-shear (rotor-stator) mixer. One sample was not treated with dispersant for use as a control. No additional suspension stabilizers such as gums or clays were added to the systems being studied. The viscosity of each final suspension was measured using a Brookfield DVII+ viscometer and a suitable spindle (LV-1, LV-2, or LV-3). To measure the effect of a dispersant, compare the viscosity of the sample with no dispersant to the corresponding sample with dispersant. The data shows that the dispersants of this invention provide viscosity reduction to the resulting agricultural compositions.

TABLE 1

Viscosity Reduction of Simazine Suspension Concentrate Samples as a function of dispersant and wetting agent

| Dispersant | Wetting Agent | Viscosity, cps | Wetting Agent | Viscosity, cps |
| --- | --- | --- | --- | --- |
| No Dispersant | SURFONIC® L24-7 | >80 | NANSA® HS90/S | 20 |
| Exp-1 | SURFONIC® L24-7 | 15.8 | NANSA® HS90/S | 16..8 |
| Exp-2 | SURFONIC® L24-7 | 22.8 | NANSA® HS90/S | 20.8 |
| Exp-3 | SURFONIC® L24-7 | 54.2 | NANSA® HS90/S | 26.8 |
| Exp-4 | SURFONIC® L24-7 | >80 | NANSA® HS90/S | >80 |

TABLE 2

Viscosity Reduction of Imidacloprid Suspension Concentrate Samples as a function of dispersant and wetting agent

| Dispersant | Wetting Agent | Viscosity, cps | Wetting Agent | Viscosity, cps |
| --- | --- | --- | --- | --- |
| No Dispersant | SURFONIC® L24-7 | >100 | NANSA® HS90/S | >100 |
| Exp-1 | SURFONIC® L24-7 | 9.2 | NANSA® HS90/S | 17.8 |
| Exp-2 | SURFONIC® L24-7 | 19.1 | NANSA® HS90/S | 21.4 |
| Exp-3 | SURFONIC® L24-7 | 12.5 | NANSA® HS90/S | >100 |
| Exp-4 | SURFONIC® L24-7 | >100 | NANSA® HS90/S | >100 |

| Dispersant designation | Anhydride Resin | Description | Polyetheramine | Description |
| --- | --- | --- | --- | --- |
| Exp-1 | SMA-1000 | 1:1 copolymer of styrene and maleic anhydride, Mn = 2000 | JEFFAMINE® XTJ-507 amine | EO/PO ratio is 6/29, nominal MW is 2000 |
| Exp-2 | SMA EF-40 | 4:1 copolymer of styrene + maleic anhydride, Mn = 4,500 | JEFFAMINE® XTJ-506 amine | EO/PO ratio is 19/3, nominal MW is 1000 |
| Exp-3 | SMA-1000 | See above | JEFFAMINE® M-2070 amine | EO/PO ratio is 31/10 |
| Exp-4 | OLOA® 15500 ashless dispersant | Polyisobutenyl-succinic anhydride | JEFFAMINE® M-2070 amine | EO/PO ratio is 31/10 |

TABLE 3

Viscosity Reduction of Captan Suspension Concentrate
Samples as a function of dispersant and wetting agent

| Dispersant | Wetting Agent | Viscosity, cps | Wetting Agent | Viscosity, cps |
|---|---|---|---|---|
| No Dispersant | SURFONIC ® L24-7 | 44.3 | NANSA ® HS90/S | >100 |
| Exp-1 | SURFONIC ® L24-7 | 24.5 | NANSA ® HS90/S | >100 |
| Exp-2 | SURFONIC ® L24-7 | 22.2 | NANSA ® HS90/S | 69.5 |
| Exp-3 | SURFONIC ® L24-7 | 58 | NANSA ® HS90/S | 43.2 |
| Exp-4 | SURFONIC ® L24-7 | 16.5 | NANSA ® HS90/S | >100 |

TABLE 4

Viscosity Reduction of Mancozeb Suspension Concentrate
Samples as a function of dispersant and wetting agent

| Dispersant | Wetting Agent | Viscosity, cps | Wetting Agent | Viscosity, cps |
|---|---|---|---|---|
| No Dispersant | SURFONIC ® L24-7 | 257 | NANSA ® HS90/S | >1000 |
| Exp-1 | SURFONIC ® L24-7 | 507 | NANSA ® HS90/S | >1000 |
| Exp-2 | SURFONIC ® L24-7 | 97 | NANSA ® HS90/S | >1000 |
| Exp-3 | SURFONIC ® L24-7 | 157 | NANSA ® HS90/S | >1000 |
| Exp-4 | SURFONIC ® L24-7 | 41.5 | NANSA ® HS90/S | 79 |

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A process for making a dispersed agricultural agent composition, comprising: mixing from about 0.5% to about 4% of a water soluble dispersant comprising a reaction product of at least one succinic anhydride-containing resin and at least one polyether monoamine with at least one water insoluble agricultural agent to form the composition.

2. The process of claim 1, wherein the agricultural agent is suspended in a fluid.

3. The process of claim 1, wherein the succinic anhydride-containing resin is selected from the group consisting of: polyisobutenyl succinic anhydride, and styrene maleic anhydride, and combinations thereof.

4. The process of claim 1, wherein the succinic anhydride-containing resin comprises at least one acrylic acid.

5. The process of claim 1, wherein the succinic anhydride-containing resin comprises a product of a monomer selected from the group consisting of: methylacrylate, and acrylonitrile, and combinations thereof.

6. The process of claim 1, wherein the composition further comprises water.

7. The process of claim 1, wherein the composition further comprises a wetting agent.

8. The process of claim 1, wherein the agricultural agent is an insecticide, a herbicide, or a fungicide.

9. The process of claim 1, wherein the dispersant has a molecular weight of from about 5,000 to about 20,000.

10. The process of claim 1, wherein the dispersant is an amic acid or a polyamic acid reaction product.

11. The process of claim 1, wherein the composition comprises from about 10% to about 50% of the agricultural agent, from about 0.5% to about 4% of the dispersant, from 0 to about 3% of a wetting agent, from 0 to about 10% of an antifreeze agent, from 0 to about 10% of an antisettling agent, from 0 to about 1% of an antifoaming agent, and the balance water.

12. The process of claim 1, further comprising: diluting the composition with water to form an aqueous composition, and applying the aqueous composition to the substrate.

13. The process of claim 12, wherein the composition is applied by spraying.

14. The process of claim 12, wherein the agricultural agent is suspended in a fluid.

15. The process of claim 12, wherein the succinic anhydride-containing resin is selected from the group consisting of: polyisobutenyl succinic anhydride, and styrene maleic anhydride, and combinations thereof.

16. The process of claim 12, wherein the succinic anhydride-containing resin comprises at least one acrylic acid.

17. The process of claim 12, wherein the succinic anhydride-containing resin comprises a product of a monomer selected from the group consisting of: methylacrylate, and acrylonitrile, and combinations thereof.

18. The process of claim 12, wherein the composition further comprises water.

19. The process of claim 12, wherein the composition further comprises a wetting agent.

20. The process of claim 12, wherein the agricultural agent is an insecticide, a herbicide, or a fungicide.

21. The process of claim 12, wherein the dispersant has a molecular weight of from about 5,000 to about 20,000.

22. The process of claim 12, wherein the dispersant is an amic acid or a polyamic acid reaction product.

23. The process of claim 22, wherein the amic acid reaction product comprises a carboxylic acid group that has been nuetralized.

24. The process of claim 22, wherein the polyamic acid reaction product comprises at least one carboxylic acid group that has been neutralized.

25. The process of claim 22, wherein the polyamic acid reaction product comprises carboxylic acid groups that have been neutralized.

26. The process of claim 12, wherein the composition comprises from about 10% to about 50% of the agricultural agent, from about 0.5% to about 4% of the dispersant, from 0 to about 3% of a wetting agent, from 0 to about 10% of an antifreeze agent, from 0 to about 10% of an antisettling agent, from 0 to about 1% of an antifoaming agent, and the balance water.

* * * * *